United States Patent
Kunze

(10) Patent No.: US 8,005,285 B2
(45) Date of Patent: Aug. 23, 2011

(54) IMAGE PROCESSING APPARATUS FOR ARTIFACT-REDUCED DETECTION OF AN OBJECT IN THREE DIMENSIONS

(75) Inventor: Holger Kunze, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 996 days.

(21) Appl. No.: 11/806,164

(22) Filed: May 30, 2007

(65) Prior Publication Data

US 2008/0005180 A1    Jan. 3, 2008

(30) Foreign Application Priority Data

May 31, 2006 (DE) .......................... 10 2006 025 402

(51) Int. Cl.
*G06K 9/00* (2006.01)
(52) U.S. Cl. .......................................... 382/131; 378/4
(58) Field of Classification Search .................. 382/130, 382/131, 154; 250/363.04; 378/4
See application file for complete search history.

(56) References Cited

U.S. PATENT DOCUMENTS

| | | | | |
|---|---|---|---|---|
| 5,485,528 A | * | 1/1996 | Horn et al. ..................... | 382/131 |
| 6,320,928 B1 | * | 11/2001 | Vaillant et al. ................... | 378/4 |
| 6,842,502 B2 | * | 1/2005 | Jaffray et al. .................... | 378/65 |
| 7,340,290 B2 | * | 3/2008 | Deimling ....................... | 600/410 |
| 2002/0133070 A1 | * | 9/2002 | Huang et al. .................. | 600/420 |
| 2003/0194119 A1 | * | 10/2003 | Manjeshwar et al. ........ | 382/131 |
| 2005/0201605 A1 | * | 9/2005 | Li et al. ......................... | 382/131 |

OTHER PUBLICATIONS

Van Lengen R., Pfeiffer M.; Bilderzeugung und Bildverarbeitung in der Medizin Studienbrief Medizinische Physik und Technik, 2. Auflage, 1997, pp. 129-132; German Office Action.

* cited by examiner

*Primary Examiner* — Jon Chang
(74) *Attorney, Agent, or Firm* — Harness, Dickey & Pierce, PLC

(57) ABSTRACT

An image processing apparatus is disclosed for generating a 3D data record from a plurality of 2D data records. The 3D data record represents an object at least partially in three dimensions, and the 2D data records respectively represent a result of a detection of the object by means of a projection through the object onto a detection plane in two dimensions. In at least one embodiment, the image processing apparatus is designed to generate the 3D data record, in particular by back projection or by filtered back projection from the 2D data records. In at least one embodiment, the image processing apparatus is designed to allocate a no object value to at least one area of the 3D data record that does not represent an object, and to allocate a changed object value to at least one area of the 3D data record in which an object location is represented by an object value.

19 Claims, 4 Drawing Sheets

IMAGE PROCESSING APPARATUS FOR ARTIFACT-REDUCED DETECTION OF AN OBJECT IN THREE DIMENSIONS

PRIORITY STATEMENT

The present application hereby claims priority under 35 U.S.C. §119 on German patent application number DE 10 2006 025 402.3 filed May 31, 2006, the entire contents of which is hereby incorporated herein by reference.

FIELD

Embodiments of the invention generally relate to an image processing apparatus for generating a 3D data record from a plurality of 2D data records. In at least one embodiment, the 3D data record represents an object at least partially in three dimensions, and the 2D data records respectively represent a result of a detection of the object by means of a projection through the object onto a detection plane in two dimensions. In at least one embodiment, the image processing apparatus is designed to generate the 3D data record, for example by back projection or by filtered back projection from the 2D data records.

BACKGROUND

An example image processing apparatus for generating 2D data records by way of projection through an object is a computer tomograph (CT) that is designed to generate at least one 2D data record by projecting an X-radiation through an object onto a detection plane, in particular a detector matrix for detecting X-radiation. Other exemplary embodiments for an apparatus for generating 2D data records by way of projection are a magnetic resonance tomograph (MRT) or ultrasonic tomograph or a positron emission tomograph (PET) or another tomograph that is designed to detect an object by way of optical projection.

Computed tomography makes available a method for detecting objects for medicine and for test engineering, and which can be used to detect internal structures of a patient or of a test object.

When an object or patient is being detected with the aid of a computer tomograph, a conical X-ray beam is projected through the object onto a detection plane, and the object is thus detected in two dimensions.

The problem arises in the case of the computer tomographs known from the prior art that the reconstruction of a 3D data record is associated with artifacts outside a detection region, also termed FOM (FOM=Focus of Measurement), that is formed as a general cut set from all the 2D detection regions, and is thus represented in all the 2D detection results. An artifact is a detection result that is not causally connected to the detected object.

In the case of computer tomographs known from the prior art, this problem is solved by way of a filtered back projection, this solution with a filtered back projection producing unsatisfactory results.

SUMMARY

In at least one embodiment, the present invention develops an image processing apparatus in such a way that the image processing apparatus does not exhibit at least one of the above-named problems.

An image processing apparatus of at least one embodiment is designed to allocate a no object value to at least one area of the 3D data record that does not represent an object, and to allocate a changed object value to at least one area of the 3D data record in which an object location is represented by an object value. The image processing apparatus of at least one embodiment is designed to generate the changed object value as a result of a predetermined assignment rule, doing so as a function of the object value representing an object location.

To this end, the image processing apparatus of at least one embodiment can advantageously have a weighting discriminator that is designed to generate a 3D difference data record that represents an object value or a no object value for each detection location.

An image quality of an object to be reconstructed can advantageously be improved by way of the allocation of a no object value or an object value as a result of a predetermined assignment rule, in particular generated by a weighting discriminator. Such a changed and therefore improved 3D data record can represent substantially fewer artifacts than detection results from computer tomographs known from the prior art.

The image processing apparatus, in particular the weighting discriminator, is preferably designed to allocate the changed object value in iteration steps as a result of a predetermined assignment rule, doing so as a function of the object value. It is advantageously possible in this way to perform a stepwise improvement of a 3D data record, for example as a function of an error or a predetermined iteration number. The 3D data record then represents the reconstructed object, advantageously with a sufficiently small error.

By way of projection, in particular by way of virtual projection, the image processing apparatus of at least one embodiment can preferably generate, from the 3D data record, virtual 2D data records that respectively represent a projection of the object represented by the 3D data record.

The image processing apparatus of at least one embodiment is further preferably designed to form, in particular in a pixelwise fashion, a difference between the virtual 2D data records and the respective corresponding 2D data records, and to generate difference 2D data records that respectively represent the difference formed.

The image processing apparatus of at least one embodiment can preferably generate by way of back projection of the difference 2D data records a difference 3D data record that represents a difference object and can add the difference 3D data record to the 3D data record, in particular in terms of voxel object points.

The 3D data record can preferably be formed by a multiplicity of voxel object points that together represent in three dimensions the object generated from 2D data records, in particular by back projection, and thus reconstructed.

In an advantageous embodiment, the image processing apparatus has an object memory for storing the 3D data record. The object memory is connected to the weighting discriminator and can be a read/write memory.

In an example embodiment, the image processing apparatus is designed to allocate, to at least one area of the 3D data record that correspondingly represents an object value greater than or equal to an absorption value of water, a changed object value that corresponds to the object value, or to allocate no changed object value.

For example, an absorption value of water is 0.18 1/cm and therefore corresponds to an absorption coefficient of water.

In the case of no changed object value a 3D data record can retain an object value, in the case of a changed object value the 3D data record is allocated an object value that corresponds to the same object value. It is thereby advantageously possible for an area of a 3D data record that corresponds to an object location to maintain its object value unchanged even when the 3D data record is varied over a number of iteration steps.

In an example embodiment of the image processing apparatus, the image processing apparatus is designed to allocate, to at least one area of the 3D data record that correspondingly represents a no object value smaller than or equal to an absorption value of air, a changed no object value that corresponds to the absorption value of air. An absorption value of air can represent an absorption coefficient of air.

It is advantageously possible in this way to set a value in the area of a 3D data record that corresponds to a smaller value than the value of air to a value that corresponds to a value of air.

In an example embodiment of the image processing apparatus, the image processing apparatus is designed to allocate an object value as a result of the predetermined assignment rule to at least one area of the 3D data record that represents an object value smaller than an absorption value of water and an object value greater than an absorption value of air.

In an example embodiment, the predetermined assignment rule represents a step function. In an example embodiment of the assignment rule, representing a step function, the image processing apparatus is designed to allocate the 3D data record a no object value when the object value is less than half the difference between the no object value and the object value that corresponds to the object value of water. The image processing apparatus is preferably further designed in such a way that the 3D data record is allocated a water value for all the object values with an object value that corresponds to more than half a difference between an air object value and a water object value.

By way of example, the 3D data record can represent values, in particular object values and/or no object values, in the form of Hounsfield units. In this embodiment, the weighting discriminator can be designed to scale the Hounsfield unit values in accordance with a predetermined, invertible scaling rule in such a way that the values represented by the 3D data record are imaged onto an interval with the interval bounds of air value and water value.

For example, the image processing apparatus of at least one embodiment, in particular the weighting discriminator, can be designed to generate changed values of a 3D data record in accordance with the following assignment rule f(value):

$$f(\text{value}) = \begin{cases} \text{air\_value}, & \text{for all values: value} \leq \text{air\_value} \\ g(\text{value}), & \text{for all values: air\_value} < \text{value} < \text{water\_value} \\ \text{value}, & \text{for all values: value} > \text{water\_value} \end{cases}$$

An air_value can be, for example, 0, a water_value can be, for example, 1. A g(value) is here a predetermined assignment rule, in particular as part of a predetermined assignment rule that is limited to an interval between an air_value and a water_value.

In an example embodiment, the predetermined assignment rule g(value) holds for the secondary condition:
g(value)<value, for all values in the interval between air_value and a starting value:
Air_value<value<starting value, and
g(value)>value for all values>starting value and all starting values in the interval between air_value and water_value:
Air_value<starting value<water_value.

A step function described in advance can run as follows for an air_value=0 and a water_value=1:

$$g(\text{value}) = \begin{cases} 0, & \text{for all values: values} \leq 0.5 \\ 1, & \text{for all values: values} > 0.5 \end{cases}$$

For example, a 3D data record can represent starting values that correspond in each case to a value of air. In another embodiment, a 3D data record can represent starting values that correspond to a first back projection of 2D data records.

In an example embodiment, the predetermined assignment rule represents at least partially a polynomial of at least the third degree, in particular the polynomial:

$$g(\text{value}) = 3 \cdot \text{value}^2 - 2 \cdot \text{value}^3.$$

In the case of air_value=0 and water_value=1, the effect of the predetermined assignment rule f (value) is that values represented by the 3D data record that are smaller than "zero" are imaged onto "zero". Values that are more than "one" remain unchanged. When they are greater than a starting value, values that lie in the interval between an air value and a water value are somewhat raised and thus are displaced in the direction of the water value. When the values are smaller than the starting value, they are displaced in the direction of air value.

Example starting values for a 3D data record, in particular for voxel object values of a 3D data record are a first back projection generated from 2D data records, or the starting value=air_value.

In an advantageous embodiment, the predetermined assignment rule represents at least one period section of a cosine function. Such a cosine function can be given, for example, by the cosine function:

$$g(\text{value}) = 1 - \text{cosine (value)}.$$

For example, a predetermined assignment rule f(value) can also have a scaling function as follows:

$$f(\text{intensity\_value}) = S^{-1}(f(S(\text{intensity\_value}))$$

wherein intensity_value represents an arbitrary intensity value of an area of a 3D data record, for example in Hounsfield units.

An area of a 3D data record can be formed by at least one voxel object point.

The abovedescribed weighting discriminator can advantageously be used to compensate artifacts based on incorrect projections in the form of 2D data records by introducing additional information relating to a material composition of an object to be reconstructed. As against the image processing apparatuses known from the prior art, which have a filtered back projection, at least one embodiment of the above-described image processing apparatus offers the advantage that only detected projection values of a 2D data record are used to reconstruct a 3D data record, and so there is no need to make an assumption in the form of an estimate for the geometric shape of an object.

Furthermore, as against known tomographs, the above-described image processing apparatus has the advantage that even materials and/or types of tissue of an object that differ from one another can be reconstructed by way of a 3D data record.

In the case of a continuous, in particular monotonically rising assignment rule g (value), there still remains in the case of subsequent iteration steps a residual measure of represented information relating to a prior value of a reconstructed area of a 3D data record, and so incorrect classifications such as occur with threshold value methods known from the prior art do not occur, thus resulting in a rapid convergence of the object represented by the iteratively changed 3D data record to the object detected by means of the 2D data records.

In an advantageous embodiment, the image processing apparatus is designed to generate the changed object value with the aid of a fuzzy unit, the fuzzy unit being able to generate the changed object value as a function of—in particular at least two—fuzzy input parameters.

Such a fuzzy input parameter can, for example, be an object value that corresponds to a predetermined material.

In an advantageous embodiment, the image processing apparatus is designed to generate the 3D data record in iteration steps in accordance with a statistical method.

Example embodiments of such a statistical method are a noise-weighted ART (ART=Algebraic Reconstruction Technique), or a statistical method in accordance with the maximum likelihood theory.

At least one embodiment of the invention also relates to a method for generating a 3D data record from a plurality of 2D data records, the 2D data records respectively representing a result in two dimensions of a detection of an object by means of projection through the object onto a detection plane, and the 3D data record representing the object at least partially in three dimensions. The method comprises the steps of:

generating a 3D data record from a plurality of 2D data records;

characterized by the steps of:

allocating a no object value in at least one area of the 3D data record by means of which no object is represented; and allocating a changed object value to at least one area of the 3D data record in which an object location is represented by means of an object value, doing so as a function of the object value as a result of a predetermined assignment rule.

In an advantageous embodiment of the method, the predetermined assignment rule represents a step function or a polynomial of at least the third degree.

A detection plane can be flat or curved. A curved detection plane is preferably cylindrically curved, and thereby forms a section of a cylinder wall.

BRIEF DESCRIPTION OF THE DRAWINGS

The invention will now be explained in more detail with the aid of figures and further example embodiments. In the drawings.

DETAILED DESCRIPTION OF THE EXAMPLE EMBODIMENTS

Figure 1:
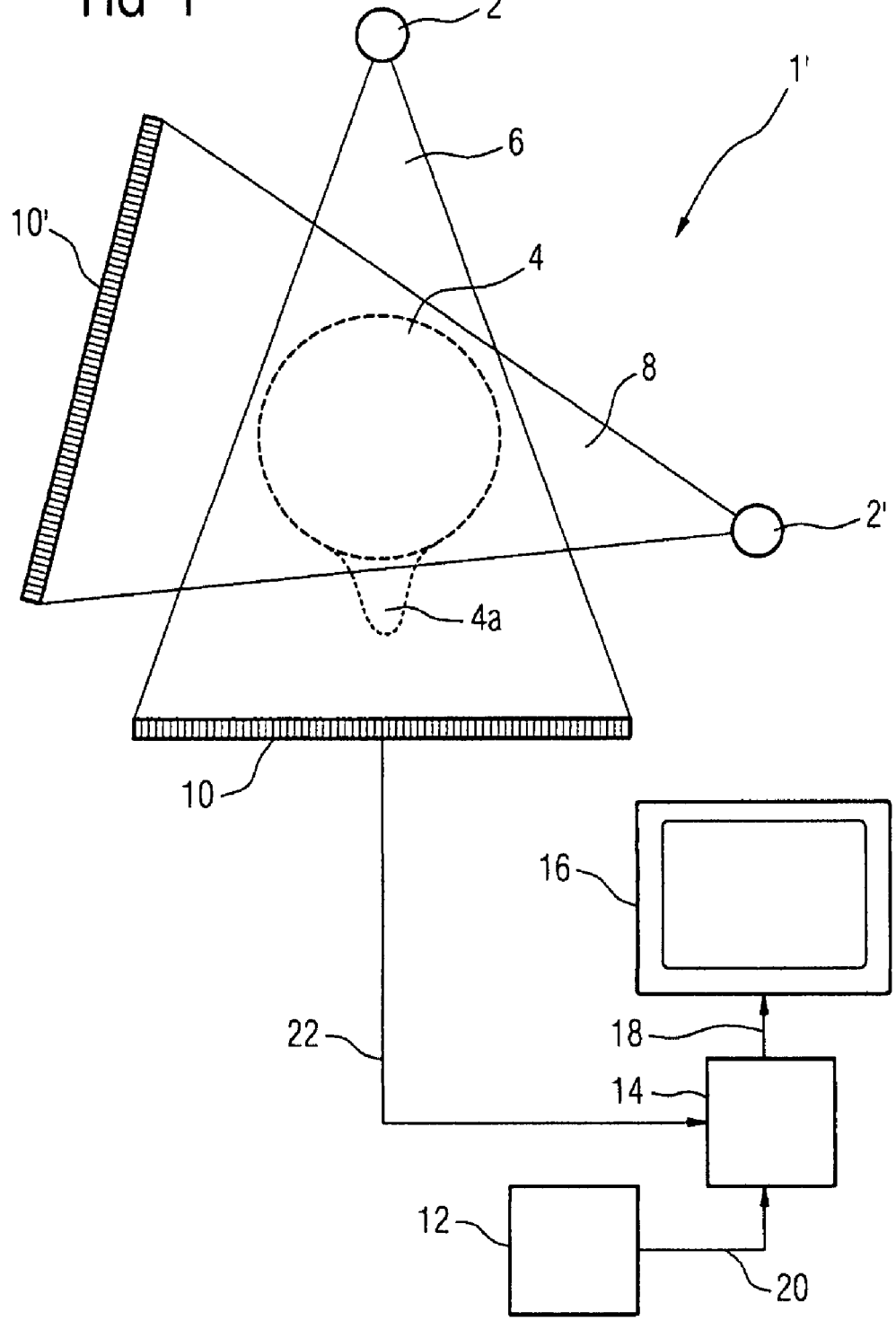
FIG. 1 shows an example embodiment of an image processing apparatus that is designed to generate a 3D data record iteratively in accordance with a predetermined assignment rule.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows an arrangement 1 for detecting an object 4 in three dimensions. The arrangement 1 comprises an X-ray source 2, the X-ray source 2 being designed to emit a conical X-ray beam 6. The arrangement 1 also comprises a detection plane 10 with a detector matrix, the detector matrix having a multiplicity of raster matrix elements.

The raster matrix elements are respectively designed to detect an X-ray and to generate an output signal corresponding to the X-ray.

The arrangement 1 also has an evaluation computer 14, an image reproduction unit 16 and a user interface 12.

The user interface 12 is connected to the evaluation computer 14 via a connecting line 20 and the image reproduction unit is connected to the evaluation computer 14 via a connecting line 18. The evaluation computer 14 is connected at least indirectly to the detection plane 10 via a connecting line 22. The detection plane 10 can be a component of a computer tomograph.

Also illustrated is the X-ray source 2 in another detection position 2'. The detection plane 10, which can be connected to the X-ray source 2 via a C arc, for example, is illustrated in another detection position 10'.

The object 4 also has an object part 4a that is located outside a common detection region in this exemplary embodiment, the common detection region being formed by an overlapping region of an X-ray beam 6 emitted by the X-ray source 2, with a beam 8 emitted by the X-ray source 2 in the position 2'. The object 4 without the object part 4a is located in the common detection region. The common detection region can be reconstructed with a low probability for the occurrence of artifacts from 2D data records generated from the detection plane 10, and so a 3D data record can be generated by the evaluation computer 14, the 3D data record representing the object 4 in three dimensions.

The object part 4a is located outside a common detection region. The object part 4a can therefore be reconstructed as part of a 3D data record only with a higher probability of artifacts to the extent that only a single filtered back projection known from the prior art can be applied in the reconstruction.

The evaluation computer 14, the user interface 12 and the image reproduction unit 16 may form an image processing apparatus. The evaluation computer 14 can have an interface—not illustrated in this figure—for connection to a computer tomograph.

The evaluation computer 14, the user interface 12 and the image reproduction unit 16 may form an image processing apparatus. The evaluation computer 14 can have an interface—not illustrated in this figure—for connection to a computer tomograph.

The evaluation computer 14 can have a weighting discriminator designed to generate a 3D data record from a plurality of 2D data records received via the connecting line 22 in accordance with a predetermined assignment rule. Via the connecting line 18, the evaluation computer 14 can output the 3D data record thus generated by reconstruction from 2D data records, doing so for the purpose of reproduction by means of the image reproduction unit 16. The generation of the 3D data record from 2D data records received on the input side via the connecting line 22 can be performed by the evaluation computer 14 as a function of a user interaction signal received via the connecting line 20.

The user interaction signal can be generated by the user interface 12, which can be designed as a keyboard, a keypad, as a touch-sensitive surface or as a trackpad, or a comparable user interface.

The evaluation computer 14 can advantageously have an FPGA apparatus or an ASIC (ASIC=Application Specific Integrated Circuit) apparatus, (FPGA=Field Programmable Gate Array).

Figure 2:
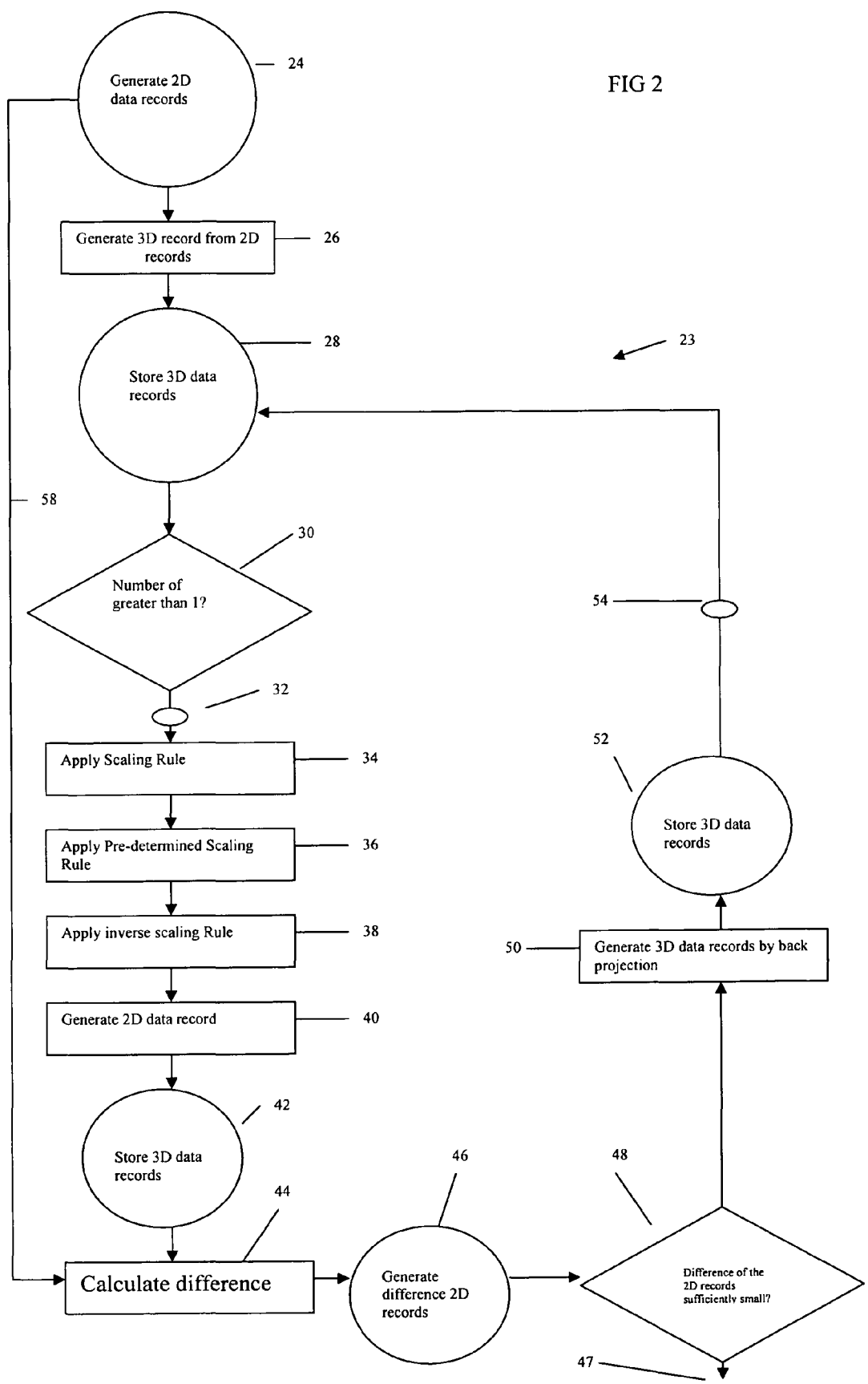
FIG. 2 shows an example embodiment of a method for generating a 3D data record that represents a reconstructed object.

FIG. 2 shows an example embodiment of a method for generating a 3D data record from a plurality of 2D data records.

In a step 24 of the method 23, an object is detected by generating 2D data records, the 2D data records respectively representing a result of a detection of the object by way of projection through the object onto a detection plane in two dimensions. In a further method step 26, a 3D data record that represents an object at least partially in three dimensions is generated from the 2D data records.

In a method step 28, the 3D data record is, for example, stored in an object memory provided therefor.

There follows in the further method an iterative method part that comprises a number of iteration steps. Iteration steps of the iterative method are partially detected in a step 30. When the number of the iteration steps is not greater than "one", the method is continued via a method step 56 of "no" in a method step 40, where at least one 2D data record is generated, a 2D data record representing a projection through a reconstructed object that is represented by the 3D data record in the current version.

The projections generated from the 3D data record of the current version are stored in a method step 42.

In a further method step 44, a difference is generated by a subtraction 58, specifically from the 2D data records generated—by detecting the object—in method step 24, and from the respectively corresponding 2D data records that have been generated in method step 40 from the 3D data record of the current version.

Generated in a further method step 46 are difference 2D data records that respectively represent the difference, detected in method step 44, between the 2D data records that represent the object in the original, and between the 2D data records that respectively represent in an examination the reconstructed object represented by the 3D data record.

In a further method step 48, a decision is made—for example by way of a discriminator—as to whether the difference represented by the difference 2D data records is small enough. If the difference is not small enough, a difference 3D data record that represents a difference object is generated by way of back projection in a method step 50 via a method step 49.

The difference 3D data record is stored in a further method step 52. The difference 3D data record stored in method step 52 is added in an addition step 54 to the 3D data record of the current version. Such addition can be performed in terms of voxel object points.

The 3D data record is formed in this embodiment by a multiplicity of voxel object points that together represent the reconstructed object in three dimensions.

The method parts formed by iteration steps can be continued in a further method step, and a decision can be made in method step 30 as a function of the iteration number as to whether a method step 34 is performed in a method step 32 of "yes". In the method step 34, the 3D data record generated in method step 28 by addition is scaled by way of a scaling rule, a value of "one" corresponding in a scaling result to an absorption quotient of water, and a value 0 corresponding to an absorption quotient of air. In a method step 36, a predetermined assignment rule f (voxel_value) is applied to the 3D data record generated in method step 34, and so a changed 3D data record is generated from the 3D data record generated in method step 34, this being done as a function of the predetermined assignment rule.

A back scaling in accordance with an inverse scaling rule is undertaken in a further method step 38, the inverse scaling rule being inverse to the scaling rule in method step 34.

In its further course, the method is continued by method step 40, in which there is renewed generation of 2D data records that respectively represent an examination projection through a reconstructed object of the current version that is represented by the 3D data record generated in method step 28.

It is possible in this way to improve the 3D data record generated in method step 28 in a stepwise fashion, that is to say iteratively, until a difference is small enough in a method step 48. If the difference is small enough in method step 48, the iterative part of the method can be interrupted in a method step 47, and the 3D data record generated in method step 28 can be output to an image reproduction unit, for example to an image reproduction unit 16 illustrated in FIG. 1. The 3D data record output to the image reproduction unit in this case represents the object detected in method step 24, in particular the original object, to a best possible approximation that has only slight artifacts, or no longer any.

Figure 3:
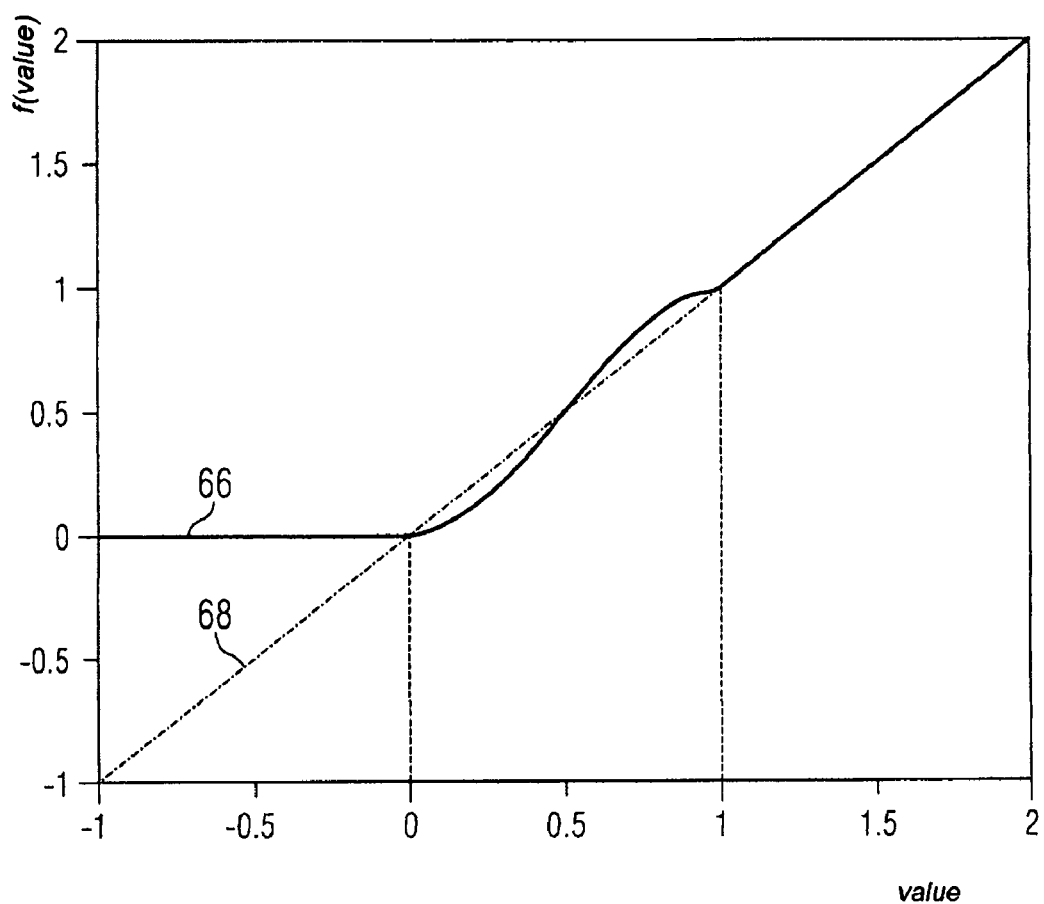
FIG. 3 shows an example embodiment of a predetermined assignment rule.

FIG. 3 is a schematic of an example embodiment of a predetermined assignment rule for generating a 3D data record from 2D data records that respectively represent a projection through an object.

Plotted on the abscissa are scaled voxel values that are respectively represented by a 3D data record. Plotted on the ordinate are changed voxel values that correspond to a result of a predetermined assignment rule. Also illustrated is the graph 66 of the predetermined assignment rule, which represents a polynomial of the third degree, at least in sections, in a definition region on the abscissa between the voxel value "0" corresponding to an air value, and the voxel value "1" corresponding to an object value.

Also illustrated is a graph 68 in the form of a dashed line, the graph 68 representing a predetermined assignment rule that corresponds to a monotonically rising function.

Figure 4:
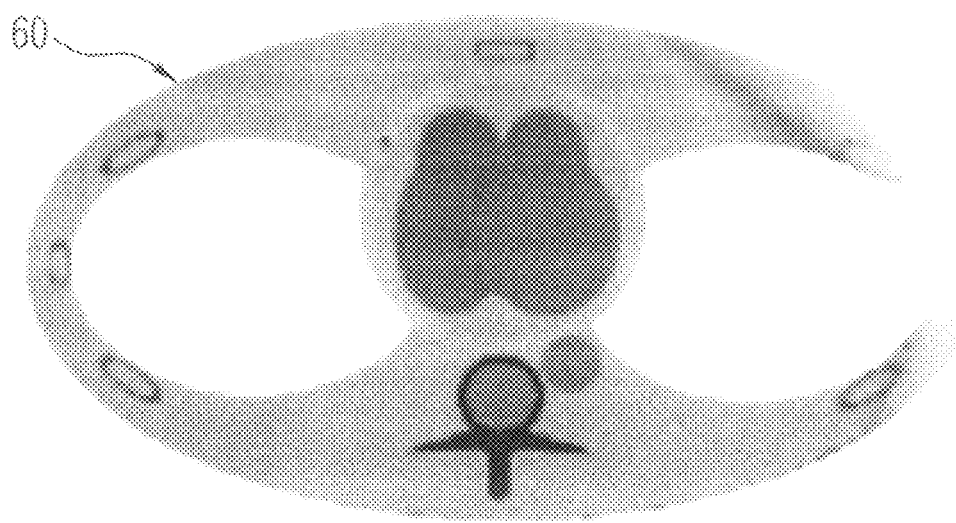
FIG. 4 shows an example embodiment of a 3D data record that represents a phantom.

FIG. 4 is a schematic of an example embodiment of a 3D data record in a sectional illustration, which represents an object in the form of a phantom thorax. It illustrates a section through the 3D data record, parallel to a transverse plane of the phantom thorax, and thus orthogonal to a sagittal plane and a frontal plane of the phantom thorax.

Artifacts are clearly to be seen in an area of the 3D data record that represents an edge of the phantom thorax.

This area, exhibiting artifacts, of the 3D data record represents a part of the object outside an FOM (FOM=Focus of Measurement). A focus of measurement is a detection area that is represented by each 2D data record of a plurality of 2D data records.

Figure 5:
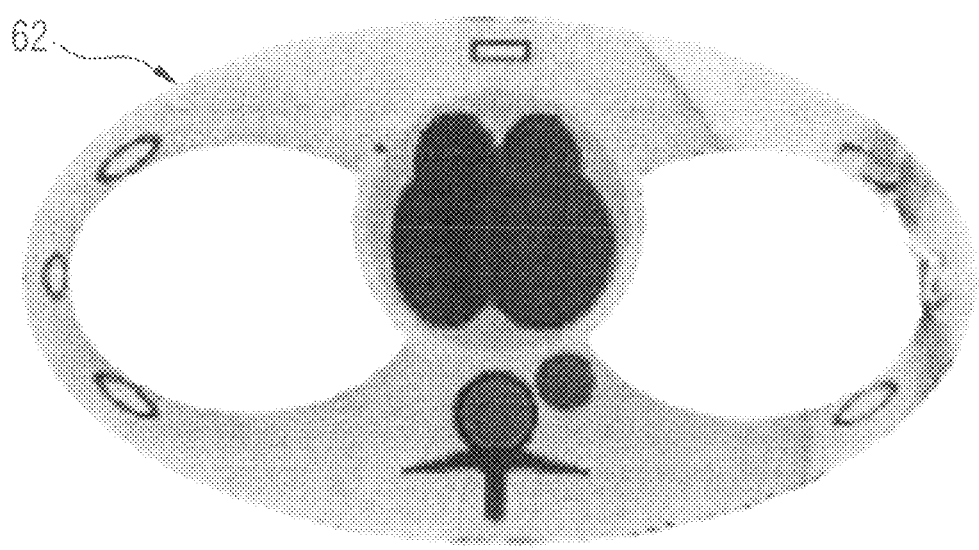
FIG. 5 shows an example embodiment of a 3D data record that represents a phantom and has been reconstructed in accordance with a predetermined assignment rule.

FIG. 5 is a schematic of an example embodiment of a section through a 3D data record that is changed by an image processing apparatus of the type described above and/or by way of a method of the type described above, in accordance with a predetermined assignment rule. A reconstructed area of the 3D data record that lies outside an FOM is clearly to be seen.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An image processing apparatus, comprising:
an evaluation unit configured to generate a 3D data record from a plurality of 2D data records, the 3D data record representing at least a portion of an object in three dimensions, and the 2D data records respectively representing a result of a detection of the object by projection through the object onto a detection plane in two dimensions, wherein, to generate the 3D data record from the plurality of 2D data records, the evaluation unit is further configured to
allocate a no object value to at least one area of the 3D data record by which no object is represented,
allocate a changed object value to at least one area of the 3D data record by which an object location is represented by the object value, wherein, to allocate the changed object value, the evaluation unit is configured to iteratively
generate the changed object value as a result of a predetermined assignment rule, the changed object value being generated as a function of the object value representing an object location,
generate virtual 2D data records from the 3D data record, the virtual 2D data records representing a projection of the object represented by the 3D data record,
calculate, in a pixelwise manner, a difference between the virtual 2D data records and corresponding 2D data records to generate difference 2D data records representing the calculated difference,
generate, using back projection of the difference 2D data records, a difference 3D data record representing a difference object, and
add the difference 3D data record to the 3D data record, the 3D data record being formed a plurality of voxel object points representing the object generated from 2D data records.

2. The image processing apparatus as claimed in claim 1, wherein the evaluation unit is configured to allocate the changed object value in iteration steps as a result of the predetermined assignment rule, doing so as a function of the object value.

3. The image processing apparatus as claimed in claim 1, wherein the evaluation unit is configured to allocate, to at least one area of the 3D data record that represents an object value that is greater than an absorption value of water or equal to an absorption value of water, a changed object value that corresponds to the object value, or to allocate no changed object value.

4. The image processing apparatus as claimed in claim 1, wherein the evaluation unit is configured to allocate, to at least one area of the 3D data record that represents a no object value that is smaller than or equal to an absorption value of air, a changed no object value that corresponds to the absorption value of air.

5. The image processing apparatus as claimed in claim 1, wherein the evaluation unit is configured to allocate an object value as a result of the predetermined assignment rule to at least one area of the 3D data record that represents an object value smaller than an absorption value of water and an object value greater than an absorption value of air.

6. The image processing apparatus as claimed in claim 1, wherein the predetermined assignment rule represents a step function.

7. The image processing apparatus as claimed in claim 1, wherein the predetermined assignment rule represents a polynomial of at least the third degree.

8. The image processing apparatus as claimed in claim 1, wherein the predetermined assignment rule represents at least one period section of a cosine function.

9. The image processing apparatus as claimed in claim 1, wherein the evaluation unit is configured to generate the changed object value with the aid of a fuzzy unit, the fuzzy unit being able to generate the changed object value as a function of fuzzy input parameters.

10. A method for generating a 3D data record from a plurality of 2D data records, the 2D data records respectively representing a result in two dimensions of a detection of an object by way of projection through the object onto a detection plane, and the 3D data record representing the object at least partially in three dimensions, the method comprising:
generating a 3D data record from a plurality of 2D data records, the generating including,
allocating a no object value in at least one area of the 3D data record by which no object is represented,
allocating a changed object value to at least one area of the 3D data record in which an object location is represented by an object value, doing so as a function of the object value as a result of a predetermined assignment rule, wherein the allocating the changed object value includes iteratively,
generating virtual 2D data records from the 3D data record, the virtual 2D data records representing a projection of the object represented by the 3D data record,
calculating, in a pixelwise manner, a difference between the virtual 2D records and corresponding 2D data records to generate difference 2D data records representing the calculated difference,
generating, using back projection of the difference 2D data records, a difference 3D data record representing a difference object, and
adding the difference 3D data record to the 3D data record, the 3D data record being formed a plurality of voxel object points representing the object generated from 2D data records.

11. The method as claimed in claim 10, wherein the predetermined assignment rule represents at least one of a step function and a polynomial of at least the third degree.

12. The image processing apparatus as claimed in claim 2, wherein the image processing apparatus is designed to allocate, to at least one area of the 3D data record that represents an object value that is greater than an absorption value of water or equal to an absorption value of water, a changed object value that corresponds to the object value, or to allocate no changed object value.

13. The image processing apparatus as claimed in claim 2, wherein the image processing apparatus is designed to allocate, to at least one area of the 3D data record that represents a no object value that is smaller than or equal to an absorption value of air, a changed no object value that corresponds to the absorption value of air.

14. The image processing apparatus as claimed in claim 2, wherein the image processing apparatus is designed to allocate an object value as a result of the predetermined assignment rule to at least one area of the 3D data record that represents an object value smaller than an absorption value of water and an object value greater than an absorption value of air.

15. The image processing apparatus as claimed in claim 2, wherein the predetermined assignment rule represents a step function.

16. The image processing apparatus as claimed in claim 2, wherein the predetermined assignment rule represents a polynomial of at least the third degree.

17. The image processing apparatus as claimed in claim 2, wherein the predetermined assignment rule represents at least one period section of a cosine function.

18. The image processing apparatus as claimed in claim 2, wherein the image processing apparatus is designed to generate the changed object value with the aid of a fuzzy unit, the fuzzy unit being able to generate the changed object value as a function of fuzzy input parameters.

19. A non-transitory computer readable medium including program segments for, when executed on a computer device, causing the computer device to implement the method of claim 10.

* * * * *